United States Patent [19]

Ford et al.

[11] Patent Number: 5,381,510
[45] Date of Patent: * Jan. 10, 1995

[54] IN-LINE FLUID HEATING APPARATUS WITH GRADATION OF HEAT ENERGY FROM INLET TO OUTLET

[75] Inventors: Dixon Ford; Steven Ford, both of Farmington, Utah

[73] Assignee: In-Touch Products Co., Woods Cross, Utah

[*] Notice: The portion of the term of this patent subsequent to Sep. 14, 2010 has been disclaimed.

[21] Appl. No.: 95,272

[22] Filed: Jul. 21, 1993

Related U.S. Application Data

[63] Continuation-in-part of Ser. No. 669,825, Mar. 15, 1991, Pat. No. 5,245,693.

[51] Int. Cl.⁶ .................... H05B 1/02; F24H 1/12; A61B 19/00
[52] U.S. Cl. .................... 392/470; 219/528; 165/170; 165/169; 165/46; 604/114
[58] Field of Search ........ 392/470, 479, 480, 485–489; 219/528; 165/170, 168, 169, 46; 604/113, 114; 137/341

[56] References Cited

U.S. PATENT DOCUMENTS

| | | | |
|---|---|---|---|
| 1,809,077 | 6/1931 | Shuman | 392/479 |
| 1,961,660 | 6/1934 | Fehrmann | 257/245 |
| 2,342,164 | 2/1944 | Pinkel | 257/245 |
| 2,424,792 | 7/1947 | Blum | 257/245 |
| 2,582,871 | 1/1952 | Kintner | 257/245 |
| 2,636,575 | 4/1953 | Watson | 183/114.2 |
| 2,690,653 | 10/1954 | Kleist | 62/126 |
| 2,766,514 | 10/1956 | Adams | 29/157.3 |
| 2,825,791 | 3/1958 | Jackson | 392/485 |
| 3,198,248 | 8/1965 | Stack | 165/166 |
| 3,293,868 | 2/1965 | Gonzalez | 62/3 |
| 3,327,776 | 6/1967 | Butt | 165/80 |
| 3,399,536 | 9/1968 | Walz | 62/3 |
| 3,443,060 | 5/1969 | Smith | 392/470 |
| 3,475,590 | 10/1969 | Pins | 392/470 |
| 3,485,245 | 12/1969 | Lahr | 128/272 |
| 3,590,215 | 6/1971 | Anderson | 392/470 |
| 3,590,917 | 11/1971 | Huber | 165/167 |
| 3,612,059 | 10/1971 | Ersek | 128/399 |
| 3,614,385 | 10/1971 | Horstmann | 392/470 |
| 3,640,283 | 2/1972 | Surindar | 128/399 |
| 3,718,182 | 2/1973 | Rosetti | 165/166 |
| 3,823,457 | 7/1974 | Staas | 29/157.3 D |
| 3,847,211 | 11/1974 | Fischel et al. | 165/166 |
| 3,853,479 | 12/1974 | Talonn et al. | 23/258.5 |
| 4,038,519 | 7/1977 | Foucras | 392/470 |

(List continued on next page)

FOREIGN PATENT DOCUMENTS

| 2112006 | 6/1972 | France | 165/46 |
|---|---|---|---|
| 2403082 | 4/1979 | France | 392/470 |

*Primary Examiner*—Bruce A. Reynolds
*Assistant Examiner*—John A. Jeffery
*Attorney, Agent, or Firm*—Workman Nydegger Seeley

[57] ABSTRACT

A disposable, in-line heating cassette and apparatus for raising the temperature of fluids. The cassette comprises a spacer defining a sinuous or serpentine flow pathway interposed between flexible foils and mounted on a frame. The frame comprises inlet and outlet tubes and related input and output ports which communicate with the serpentine path. Juxtaposed heating plates in direct contact with the cassette substantially contact the entire heating surface of the foils, providing a highly efficient thermal path from the heating plate to the foil, and then to the fluid. The heating blocks have several electrically conductive strips thereon for generating a gradation of heat energy such that more heat energy is available for transfer at the inlet end than the outlet end of the serpentine flow path. The strips are arranged on the heating plates immediately over and under the serpentine flow path and are divided into contiguous perpendicular sections, each section having a corresponding closest parallel section with a conductor separation distance therebetween.

61 Claims, 6 Drawing Sheets

Microfiche Appendix Included
(1 Microfiche, 80 Pages)

U.S. PATENT DOCUMENTS

| | | | |
|---|---|---|---|
| 4,108,146 | 8/1978 | Golden | 128/400 |
| 4,167,663 | 9/1979 | Granzow, Jr. et al. | 219/497 |
| 4,258,784 | 3/1981 | Perry | 165/166 |
| 4,287,883 | 9/1981 | Kyrias | 126/445 |
| 4,293,762 | 10/1981 | Ogawa | 392/470 |
| 4,309,592 | 1/1982 | Le Boeuf | 219/299 |
| 4,314,143 | 2/1982 | Bilstad | 219/497 |
| 4,356,383 | 10/1982 | Dahlberg et al. | 392/470 |
| 4,464,563 | 8/1984 | Jewett | 392/470 |
| 4,532,414 | 7/1985 | Shah | 392/470 |
| 4,540,412 | 9/1985 | Van Overloop | 604/291 |
| 4,574,876 | 3/1986 | Aid | 165/46 |
| 4,678,460 | 7/1987 | Rosner | 604/113 |
| 4,680,445 | 7/1987 | Ogawa | 392/470 |
| 4,707,587 | 11/1987 | Greenblatt | 392/470 |
| 4,731,072 | 3/1988 | Aid | 604/408 |
| 4,744,414 | 5/1988 | Schon | 165/167 |
| 4,759,749 | 7/1988 | Verkaart | 604/113 |
| 4,782,212 | 11/1988 | Bakke | 392/470 |
| 4,801,777 | 1/1989 | Auerbach | 219/10.55 |
| 4,844,074 | 7/1989 | Kureuz | 128/401 |
| 4,847,470 | 7/1989 | Bakke | 392/470 |
| 4,878,537 | 11/1989 | Verkaart | 165/156 |
| 4,906,816 | 3/1990 | Van Leerdam | 392/470 |
| 4,908,014 | 3/1990 | Kroyer | 604/4 |
| 4,919,134 | 4/1990 | Streeter | 128/400 |
| 4,938,279 | 7/1990 | Betker | 165/46 |
| 4,962,761 | 10/1990 | Golden | 128/400 |
| 4,966,231 | 10/1990 | Belcher | 165/166 |
| 4,971,056 | 11/1990 | Seacord | 128/401 |
| 5,125,069 | 6/1992 | O'Boyle | 392/465 |
| 5,245,693 | 9/1993 | Ford et al. | 392/470 |

IN-LINE FLUID HEATING APPARATUS WITH GRADATION OF HEAT ENERGY FROM INLET TO OUTLET

This application is a continuation-in-part of the parent application U.S. Ser. No. 07/669,825, filed Mar. 15, 1991, now U.S. Pat. No. 5,245,68 which is incorporated herein by reference.

Appendix A referred to herein, may be found in the microfiche appendix contained in the PTO file for this patent document. The microfiche appendix is comprised of one microfiche having 80 frames.

A portion of the disclosure of this patent document: contains material to which a claim of copyright protection is made. The copyright owner has no objection to the reproduction by anyone of the patent document or the patent disclosure as it appears in the Patent and Trademark Office patent file or records, but reserves all other rights with respect to the copyrighted work.

BACKGROUND

1. Field of the Invention

This invention relates to in-line fluid heating apparatus and more specifically to an apparatus for warming parenteral fluids such as blood.

2. Background Art

Blood and other parenteral fluids are commonly stored at hypothermic temperatures in the range of about 2° −10° C. to maintain freshness and viability. Before such fluids are infused into a patient, it is common practice to raise the influent fluid temperature to nearly normal patient temperature levels of 36°–38° C. This is sometimes done by using water baths to warm several individual units or bags of blood simultaneously. In some cases, such as open heart surgery, it is desirable to maintain the patient at hypothermic temperatures for a period of time and infuse blood at substantially the same hypothermic temperature. As such infusions vary in rate and temperature, it is best to have in-line blood warming devices which warm the blood as delivery is made from a blood bag to the patient to conserve blood and reduce delays of off-line heating methods, such as water baths.

The rate of caloric exchange and thus the rate at which a fluid such as blood is warmed is proportional to the temperature differential between a heat emitting surface and the blood, for a given increment of time. This means that, theoretically, a fluid at zero degrees may absorb 100 calories per second when in contact with a surface maintained at 100 degrees. Similarly, a fluid at 50 degrees will absorb 50 calories per second when contacting the same 100 degree surface, and a fluid at 90 degrees will absorb only 10 calories per second when contacting that same surface. Thus, a fluid such as blood is warmed at the inlet of an in-line fluid warming device it will absorb more heat than at the outlet since it becomes warmer as it travels through the device. Accordingly, a complication in the warming of viable physiological fluids, such as blood, is a maximum safe temperature which may be used in the heating process. It is commonly known that the maximum safe temperature which may be used is in the range of 38° C. This tends to impose serious constraints in some situations. For example, in emergency cases where a patient has lost large quantities of blood, the blood must be replaced quickly by rapid infusion. However, it is very difficult to warm such large quantities of blood to the desired temperatures rapidly enough using in-line blood warmers.

Since the blood which exits an in-line blood warmer must typically be 36°–38° C., where large quantities of blood are required very quickly as in causes of severe trauma and blood loss, the temperature of the warming apparatus is typically elevated above the 36°–38° C. range because heat transfer must take place more rapidly. Thus, by increasing the temperature, as the cool blood first enters the in-line warming apparatus, it will be more rapidly warmed. However, it is very difficult to maintain the proper temperatures at both the inlet and the outlet. If the temperature is too high, the outlet blood temperature may be proper but the blood may be damaged by the high temperature at the inlet as it is first heated. If the temperature is lowered, damage to the blood at the inlet may be avoided, but the desired outlet temperature may not be achieved. To date, these and other problems in the art have not been adequately solved.

BRIEF SUMMARY AND PRINCIPAL OBJECTS OF THE INVENTION

The present invention is an in-line fluid warming apparatus. More specifically, the inventive concepts embodied in the present apparatus have been specifically designed for application in the context of an in-line fluid warming apparatus used for delivery of parenteral fluid, such as blood, without the problems noted above.

The apparatus comprises, in a preferred embodiment, a disposable cassette which is attachable to inlet and fluid delivery lines. The cassette is comprised of an insulating spacer that defines a sinuous or serpentine flow path. Flexible metallic foil is bonded to the top and bottom of the spacer, thereby enclosing the serpentine flow path. The spacer and top and bottom foils are secured by a plastic frame that holds the entire assembly. The cassette, as thus constructed, is attached at inlet and outlet ports provided in the frame to tubing through which the parenteral fluid, such as blood, enter the cassette, and then is delivered after being warmed, to the patient.

The apparatus further comprises a housing into which the cassette is inserted. The housing contains microprocessor-controlled heating means that provide heat transfer to the top and bottom foils. An instrument panel on the apparatus permits selection of a set point temperature and display of the actual output temperature of the warmed fluid.

In one important aspect of the invention, the heating means comprise heating plates that are warmed by one or more thin electrically conducting heating wires or strips which apply a decreasing heat gradient of power watt density over the entire area of the heat plates, such that more energy is available to the flowing parenteral fluid at the inlet end than at the outlet end. The combination of one heating block and one series of electrical conducting wire backed by an insulating layer represent a heating unit or element. One heating unit is fixed while the other is insertable to permit easy insertion and clamping of the disposable blood warming cassette.

Heating is accomplished by placing the metallic foils in relatively high pressure contact with the heating plates which are heated to a temperature required to warm fluid to a selected set point. Full contact between each foil and heating plate is assured by providing an upstream pressure on the fluid at the inlet such that each foil is forced outward above the serpentine path against each heating plate, thereby enhancing the contact area between the foil and each heated plate. Each set point temperature to which fluid is heated is user variable and is set in a range from hypothermic temperatures for hypothermically maintained patients to nearer normal physiological temperatures in the range of 36° C.–38° C. The apparatus preferably is provided with controls to ensure that a set point temperature can be entered which the fluid temperature will not exceed, such as a predetermined maximum temperature of 38° C., depending on the procedure.

Higher than ambient internal pressure in the cassette not only assures a full and pressured contact against each heating plate, but also reduces the generation of outgassing bubbles which may otherwise occur due to negative pressures resulting from gravity-caused deformations in flexible parts. The elimination of outgassing allows the cassette to be oriented for use in any plane. Use of fluid contacting, heat conducting foils in direct pressure contact with the heating plates provides a fluid warmer of surprising efficiency.

The heating plates preferably have a constant thermal mass and constant dimensions in cross section, and have exothermic heating elements thermally associated therewith which produce greater heat output capacity in areas where heat transfer is the greatest. In addition, the heating elements preferably have electrical connections and are contained with the heating plates in plate holders having side rails providing insertion guides, whereby each plate is releasably inserted into the instrument housing and thereby electrically connected as a modularly replaceable part.

The instrument provides housing and control for the cassette and heating plates. The instrument also comprises temperature and status displays and switches on a control panel that serves as a user interface. The instrument housing comprises a top plate guide that is reciprocally operated to raise and lower the top heating plate so as to release and apply pressure between the heating plates between which the cassette is situated. Thereby, a cassette is easily inserted and firmly held in position while parenteral fluid is passed through it and heated.

In accordance with the foregoing, it is a primary object of the present invention to provide an in-line fluid warming apparatus capable of accurately controlling in-line fluid temperatures, particularly when rapid infusion is required to be delivered by the apparatus.

A further object of the invention is to provide an in-line fluid warming apparatus for delivering parenteral fluids to a patient at accurately controlled temperatures, even during rapid infusion.

A related object of the invention is to provide an in-line fluid warming apparatus having a disposable cassette insertable between a pair of heating plates, and wherein the cassette provides a long, thin flow path between two metallic foil layers, and the heating plates have a heating strip arranged to provide an essentially linear power density decrease along the flow path, which in combination provides a highly controlled heating profile and accurately controlled fluid temperature at high volumetric flow rates.

Additional objects and advantages of the invention will be set forth or obvious from the description which follows, or may be learned by the practice of the invention. The objects and advantages of the invention may be realized and obtained by means of the instruments and combinations particularly pointed out in the appended claims.

BRIEF DESCRIPTION OF THE DRAWINGS

In order to more fully understand the manner in which the above-recited and other advantages and objects of the invention are obtained, a more particular description of the invention briefly described above will be rendered by reference to the presently understood best mode for making and using the same, as illustrated in the appended drawings. Understanding that these drawings depict only typical embodiments of the invention and are therefore not to be considered as limiting of its scope, the invention will be described with additional specificity and detail through the use of the accompanying drawings in which.

DETAILED DESCRIPTION OF THE PREFERRED EMBODIMENTS

Figure 1:
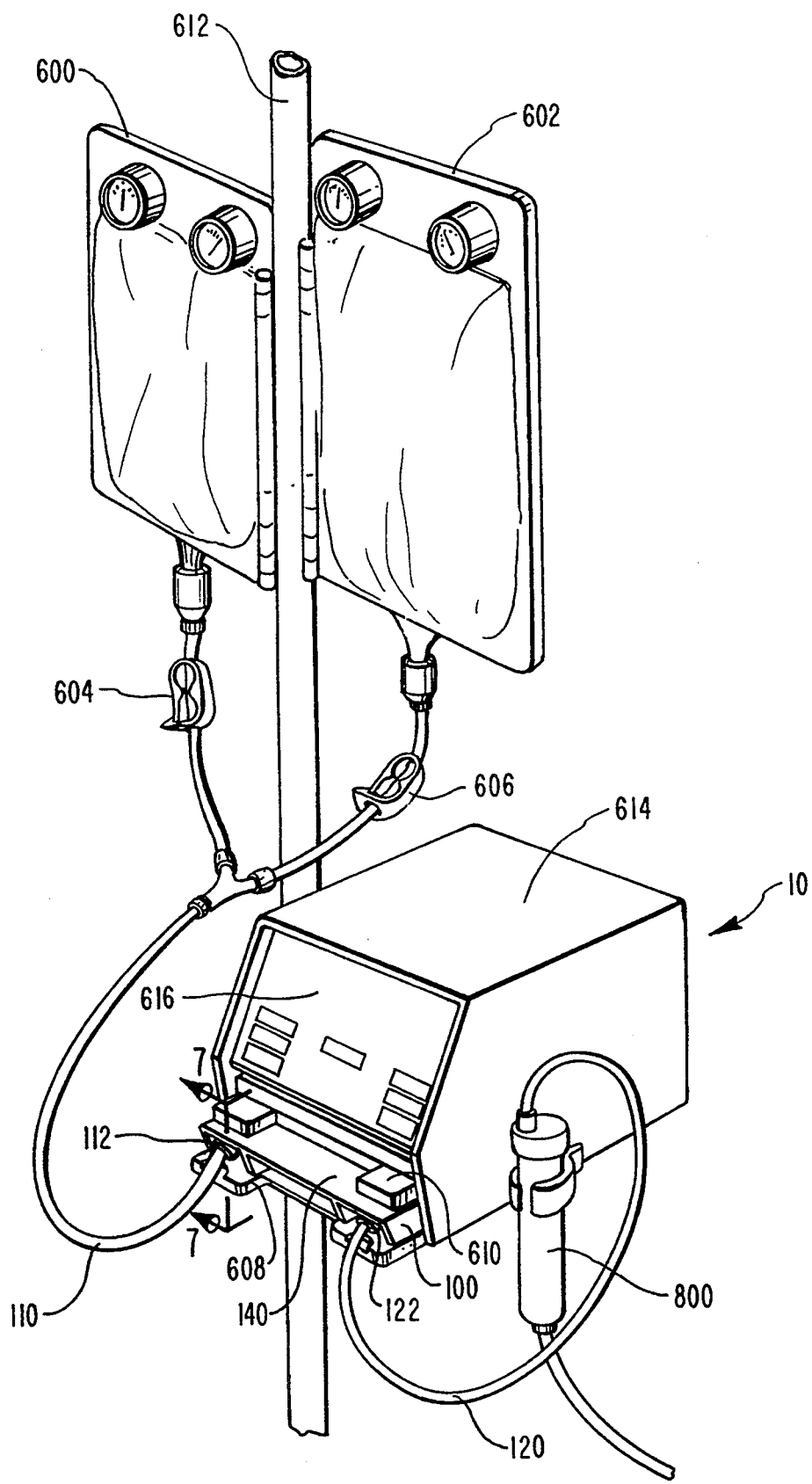
FIG. 1 is a perspective of a fluid heating assembly and associated housing and control apparatus showing major operational components.

In this description, the term proximal is used to indicate the segment of the device normally closest to the operator when it is seen or being used. The term distal refers to the other end. Reference is now made to the embodiment illustrated in FIGS. 1–7 wherein like numerals are used to designate like parts throughout. A currently preferred embodiment of the invention as designed for warming a parenteral fluid is generally designated at 10 in FIG. 1. The apparatus 10 is mounted on I.V. pole 612. Parenteral fluid, for instance blood, is stored in bags enclosed within automatic pressure devices 600, 602, which serve to pressurize the blood. Tube clamps 604, 606 regulate the flow rate of pressurized blood to the parenteral fluid heating assembly 10.

The present invention also contemplates that fluid introduced to the parenteral fluid heating assembly 10 may be a gaseous substance, in cases where gas is to be heated for intracorporeal delivery. By way of example, and not by waxy of limitation, the parenteral fluid heating assembly 10 may receive gaseous carbon dioxide from a gas source to pre-heat the gas for insufflation of a patient's abdomen for gall bladder surgery. Therefore, all references to fluid are intended to mean either a liquid or a gas. Furthermore, while the presently preferred embodiment has been designed for delivery of parenteral fluids, specifically blood, the inventive concepts of the apparatus may also be usefully employed in other medical or industrial applications.

Figure 2:
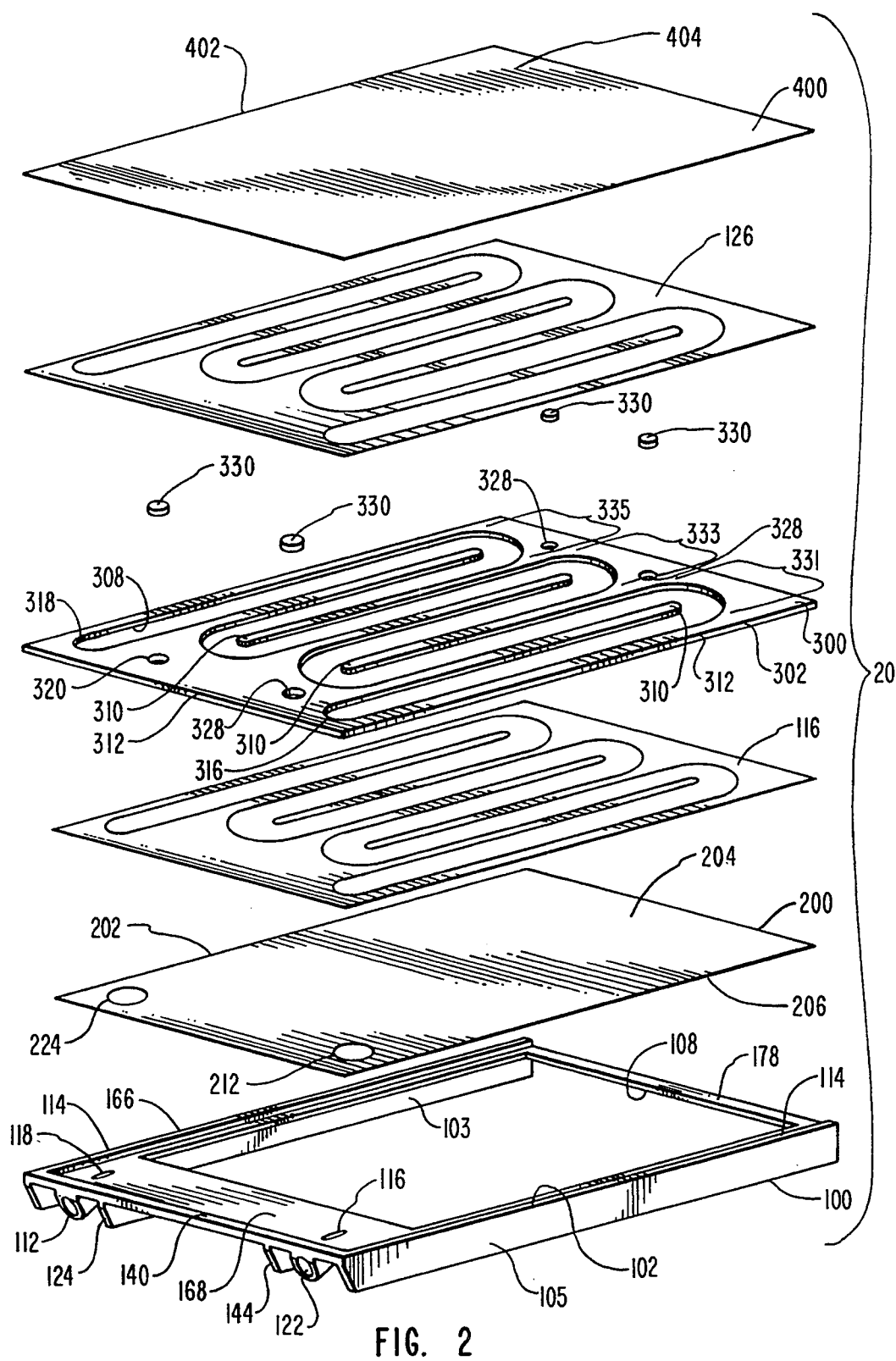
FIG. 2 is an exploded perspective of the cassette wherein six layered parts are seen.
Figure 7:
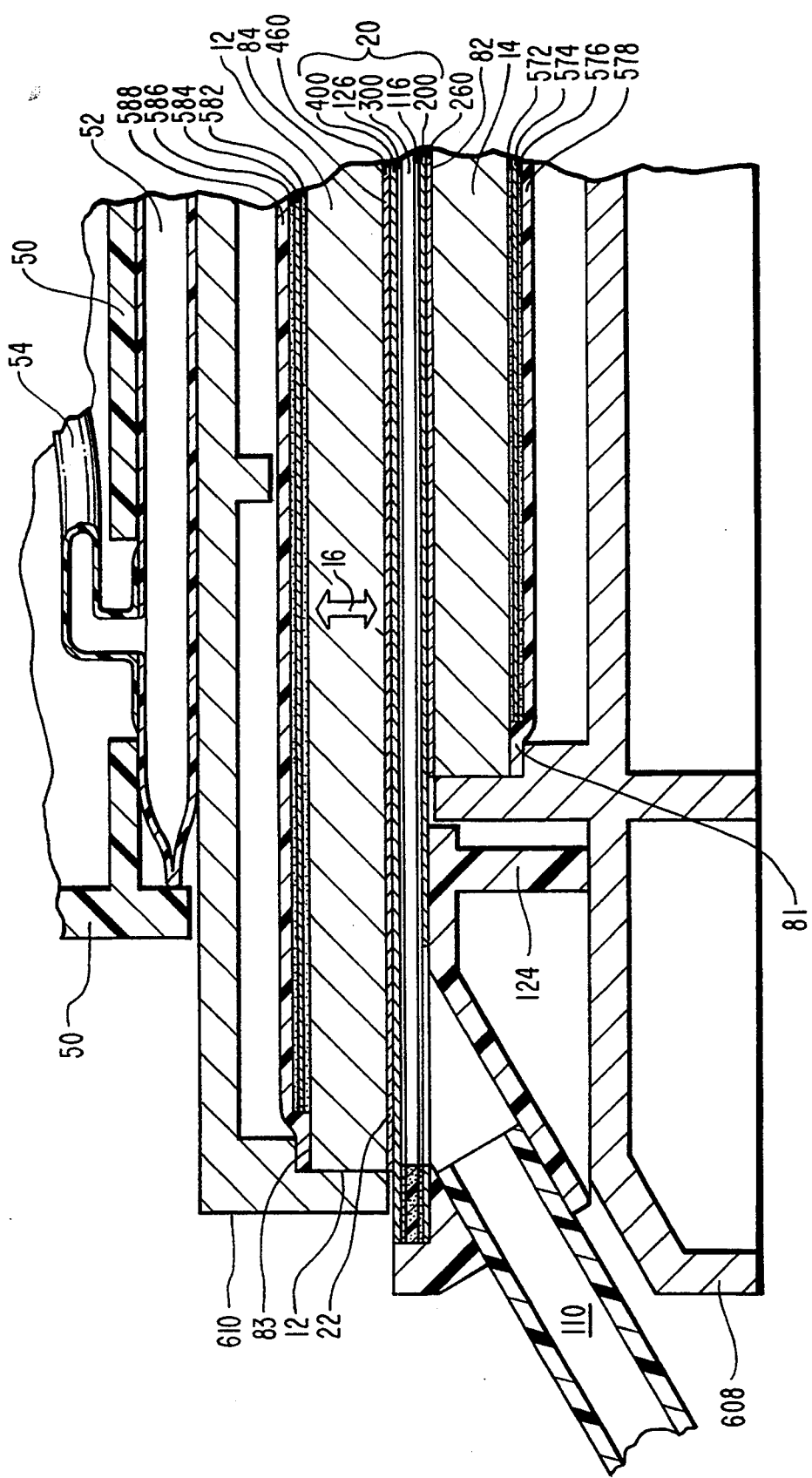
FIG. 7 is a sectional view along lines 7—7 of FIG. 1.

Enclosed within the fluid heating assembly 10 is a cassette means for transferring heat to fluids flowing therethrough. By way of example and illustration of the same, a fluid heating cassette 20 is shown in FIGS. 2 and 7. The fluid heating cassette 20, as shown in FIG. 7, is disposed between an upper heating plate 12 and a lower heating plate 14.

As shown best in FIG. 2, the cassette means comprises a passageway means for defining a thin, planar, elongated, sinuous flow path having top and bottom sides and an inlet end and an outlet end, such that a thin sheet of fluid enters the inlet end, travels through the flow path, and exits an outlet end. By way of illustrating such passageway means, FIG. 2 shows a spacer 300 defining a flow path 308.

The cassette means further comprises first and second flexible, heat conductive membrane means supported by the passageway means on one of the top and bottom sides of the flow path 308 for providing heat transfer to fluid in the flow path 308. To illustrate the preferred embodiment, an example of the first and second membrane means is seen in FIG. 2 as flexible foils 200, 400.

The cassette means further comprises a support means for providing a framework that sealingly receives and holds the first and second heat conductive membrane means with the passageway means. As an illustration and example of the support means, frame 100 is depicted in FIG. 2.

Figure 5:
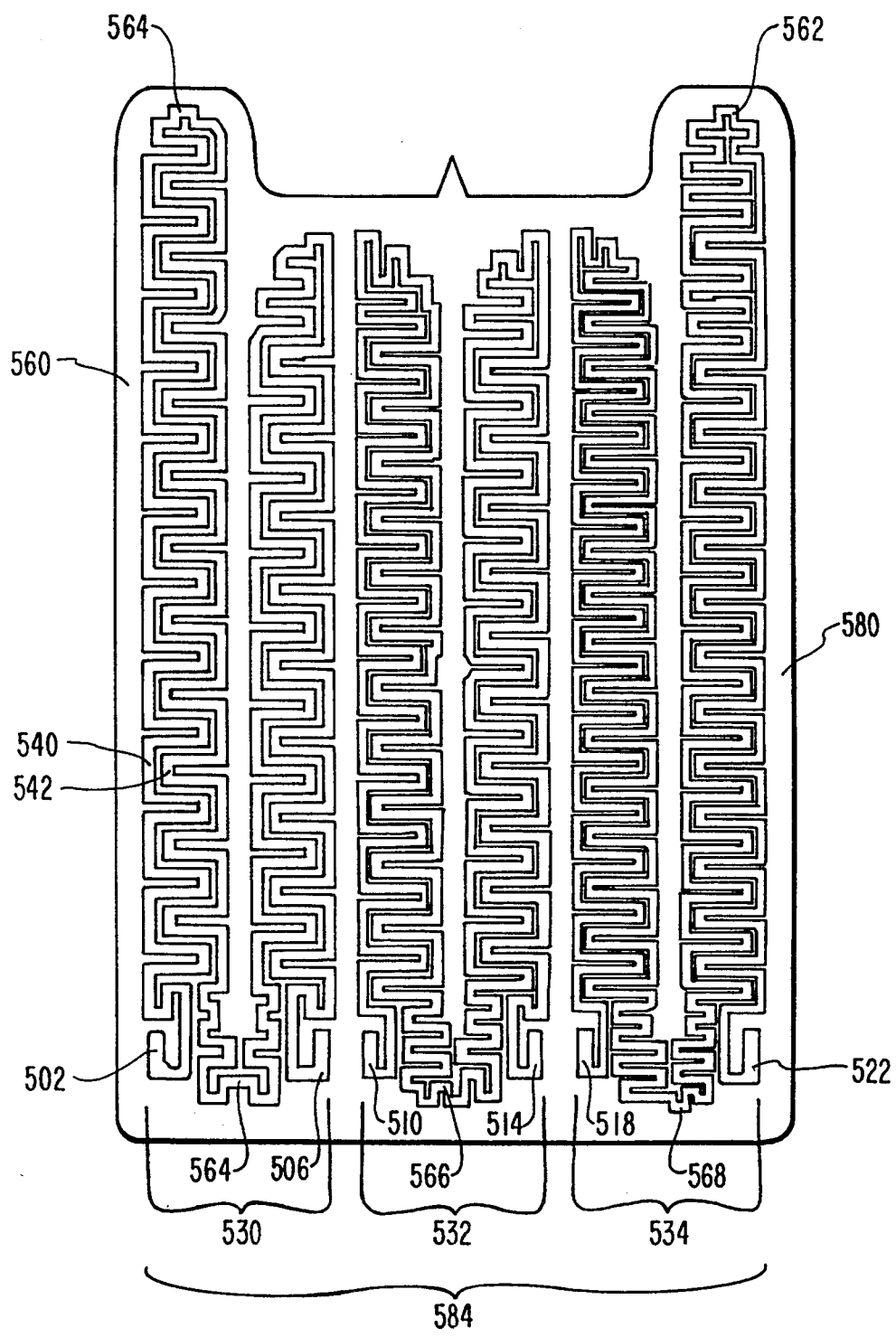
FIG. 5 is a top plan view of the top heating plate layered with a flexible film heater layer enclosing an electrically conductive strip.
Figure 6:
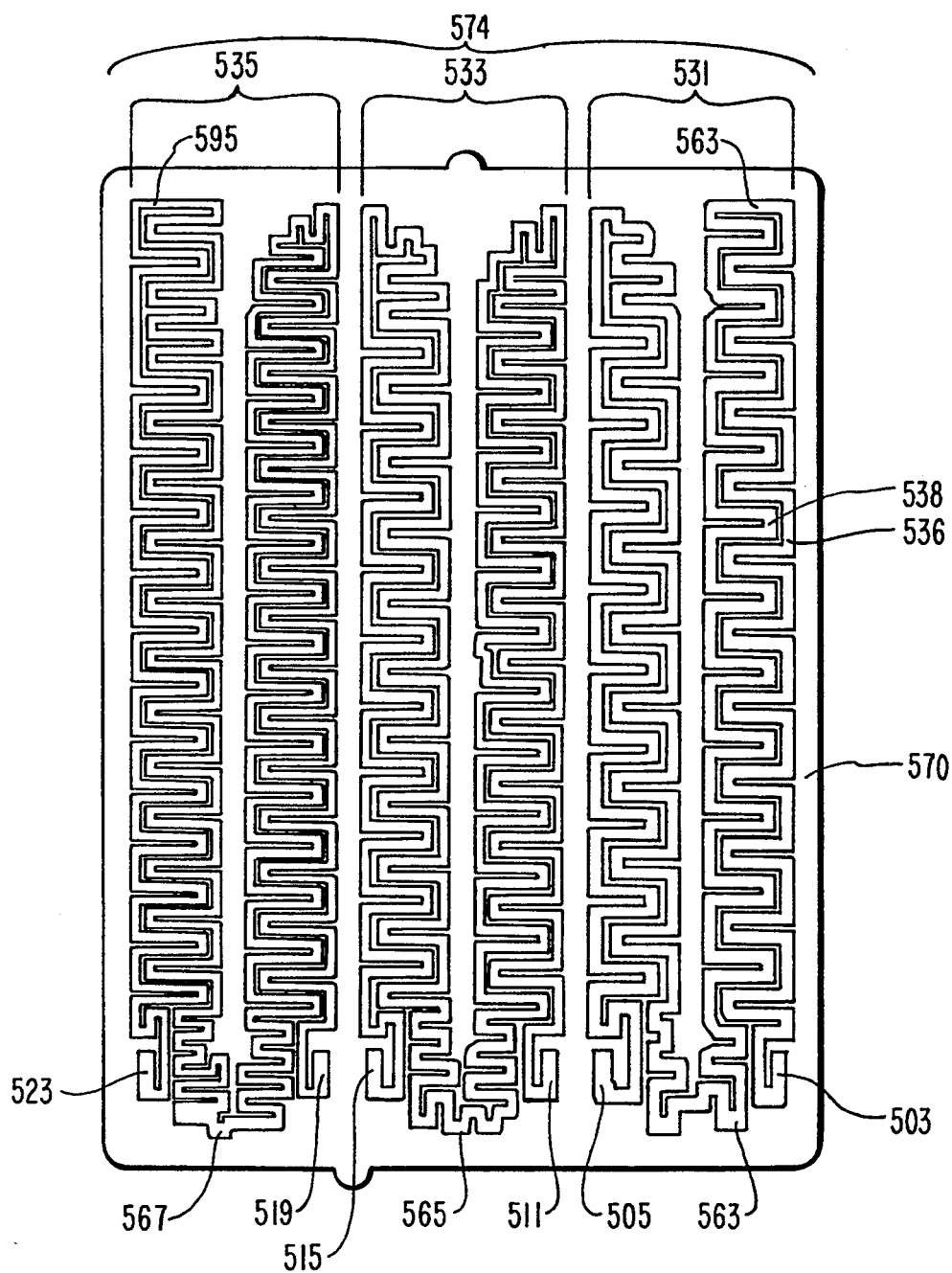
FIG. 6 is a bottom plan view of the bottom heating plate layered with a flexible film heater layer enclosing an electrically conductive strip.

The apparatus for heating fluids further comprises a heating means in contact with at least one of the first and second membrane means for generating heat energy that is transferred to the fluid in the flow path 300. The heating means comprises a heating element means having a shape that is essentially a mirror image of the flow path, for generating and transferring a gradation of heat energy to the fluid in the flow path 308. The heating element means is disposed essentially both vertically offset from and in alignment with at least one of the top and bottom sides of the elongated sinuous flow path. To show a preferred embodiment of the invention and as an example thereof with respect to the heating means, heating plates 12 and 14 are depicted in FIG. 7. Similarly, an example of the heating element means is seen in FIGS. 5, 6, and 7 as heat conductive strips 574 and 584.

Cassette 20 is in thermal communication with heating plates 12 and 14 through direct contact between heating plates 12 and 14 and foils 200, 400 which are also in direct contact with the fluid flowing through path 308 as is described in detail hereafter. Fluid enters into cassette 20 through inlet tube 110 (see FIG. 1) and exits toward an infusion site through outlet tube 120. Inlet tube 110 and outlet tube 120 are firmly sealed to cassette 20 by adhesives or other bonding agents. Tubes 110 and 120 may be vinyl tubes commonly used in medical IV applications. Adhesives and other bonding agents for affixing vinyl tubes to other synthetic resinous materials are well known and available in the art. As is common practice when infusing intravenous fluids, a bubble trap 800 is disposed between a patient and the cassette 20 when in use.

Cassette 20 is comprised of at least four parts, frame 100, a lower heat transmitting layer or foil 200, spacer 300, and an upper heat transmitting layer or foil 400, as seen in FIG. 2. Frame 100 provides structural support for the other parts of cassette 20. As is best seen in FIG. 2, frame 100 comprises a distal support 178, a first side member 102, a second side member 166, and a proximal support 168. Disposed on either side of proximal support 168 is right bottom plate stop 144 and left bottom plate stop 124, both of which serve as a stop and alignment for bottom plate 14. The frame 100 further comprises ledge 114, input ports 112, 118, output ports 122, 116, distal support bottom side 108, right frame alignment rail 105, and left frame alignment rail 103.

The top heating plate 12 projects so as to overlap both the fluid inlet point 118 and the outlet point 116 as shown in FIG. 7. Bottom plate 14, when installed within the fluid heating assembly 10, is aligned within frame 100 by resting against proximal support 168, right bottom plate stop 144, left bottom plate stop 124, distal support bottom side right frame alignment rail 105, and left frame alignment rail 103. The two supports 103, 105, in combination, provide a guide for inserting cassette 20 into a position of use as is described in detail later. Frame 100 is fabricated by molding or machining from rigid, synthetic resinous material which is essentially inert to parenteral fluids. A material such as cyrolyte may be used for frame 100.

Frame 100 comprises an attachment port 112 for inlet tube 110. Attachment port 112 is sized and shaped to accept plastic inlet tube 110, as seen in FIG. 1. Plastic inlet tube 110 is selected from materials generally used for parenteral fluid transport in medical practice. Similarly, frame 100 further comprises an attachment port 122 for outlet tube 120. Tube 120 is essentially the same tubing material as inlet tube 110. Ports 112, 122 each feature an obtuse angle flow path.

As seen in FIGS. 2 and 7, a thin foil, which may be metallic or other material which is highly thermally conductive and essentially inert to physiological fluids provides a first heat conductive layer 200. Such a layer 200 may be silver plated copper or other such highly conductive materials, but for parenteral fluids is preferably stainless steel foil. Such a stainless steel foil may be in the range of 0.0001 to 0.010 inches (0.0025–0.254 mm) thick. Layer 200 comprises a rectangular shape having a top surface 204, perimeter 202, and a bottom surface 206. The bottom surface 206 is compressively bonded with and is attached to frame 100 by an adhesive applied at predetermined sites.

The bottom flexible foil 200 fits within the confines of ledge 114, thus placing the bottom flexible foil 200, which is also physiologically inert, onto the frame 100 so as to contact the predetermined sites that are previously treated with adhesive, and so as to nest in and against the ledge 114. The perimeter 202 of layer 200 comprises a shape which nests within ledge 114 when layer 200 is juxtaposed to frame 100. The height of ledge 114 is greater than the thickness of layer 200. Layers 200, 400 may be in the range of 0.0001 to 0.010 inches (0.0025–0.254 mm) in thickness, while the depth of ledge 114 may be in the range of 0.035 inches (0.889 mm). To attach layer 200 to frame 100, layer 200 is nested on surface 144 within the perimeter of rim 106. When disposed thereat and firmly attached thereto, orifice 224 is juxtaposed to and aligned with orifice 118 and orifice 212 is juxtaposed to and aligned with orifice 116, thus providing continuous fluid pathways.

A unitary member or spacer 300 which also defines flow path 308 is seen in FIGS. 2 and 7. As seen in FIG. 2, spacer 300 is a planar member of essentially uniform thickness, and defines a serpentine path 308 having a thickness of an edge 302. By way of example, the width is approximately 0.625 inches (0.16 mm) and the thickness of edge 302 is in the range of 0.040 inches (0.01 mm). The part is formed by stamping or machining and then is subsequently deburred to eliminate any rough edges where blood or other biologically active fluids may accumulate and react.

Spacer 300 is made from physiologically inert materials which adhesively attach to layer 200 and layer 400. Such materials are known and available in the art, however, a preferred embodiment is a foam material which better compensates for the absence of completely flat surfaces in plates 12 and 14. Spacer 300 comprises an outer perimeter 312 of essentially the same shape and size as that of foil layer 200 such that spacer 300 also nests within ledge 114 when spacer 300 is juxtaposed and aligned with foil layer 200.

The apparatus of the present invention preferably allows the fluid in the passageway 308 to receive thermal energy from two opposing directions at all points in the passageway 308. Thus, fluid surface area in the fluid passageway 308 will make contact with only one foil at a time. In essence, the unitary member or spacer 300 keeps the two thermally conductive membranes or metallic foil sheets 200, 400 completely separate and out of contact with each other at all points within the cassette. Due the presence of the spacer 300, there are no junction points where the two foils meet. The object of this preferred embodiment is to conduct heat exchange from the two foils 200, 400 by simultaneously heating the volume of fluid from two opposing directions so as to both rapidly and controllably heat the fluid, even during rapid infusion. It is preferable to keep the two flexible, heat conductive foils 200, 400 separate and apart.

As seen in FIG. 2, spacer 300 comprises a mostly open medial section providing a serpentine flow passageway 308. A series of path separators 310 extend proximally and distally to separate and effectively lengthen the fluid flow path. In cross section, path separators 310 may be in the range of three-sixteenths (0.048 mm) of an inch wide and 0.040 (0.01 mm) inches high. The disposition of the separators 310 within spacer 300 provides a pathway in the range of five-eighths (0.16 mm) of an inch wide and 0.090 (0.0225 mm) inches high. The serpentine flow passageway 308 has three sections called flow path zones. The third flow path zone 331 of the passageway 308 is the last section of the passageway before the fluid therein exits the passageway 308. The second flow path zone 333, is the middle section of the passageway 308, and the first flow path zone 335 is the section of the passageway 308 that the fluid first travels along when it enters the passageway 308.

A top layer 400, seen in FIGS. 2 and 7, is placed and affixed by adhesive 126 to spacer 300 to provide a topmost containment. Bottom layer 200, seen in FIGS. 2 and 7, is placed and affixed by adhesive 116 to spacer 300 to provide a bottom most containment. Thus, foil layer 200 and foil layer 400 are adhesively attached to spacer 300 thereby forming the contained serpentine path 308 wherein the fluid is heated.

In a preferred embodiment of manufacturing the cassette 20, top and bottom flexible foils 400, 200, are placed in contact with a heated surface (not shown) having a high temperature. The spacer 300 is preferably constructed as a unitary member made of a resilient foam (polyethylene) or other material having similar melt characteristics, and is placed in contact with and between the top and bottom foils 400, 200 so as to nest in and against the ledge 114. Next, the foam spacer 300 is compressed between the heated foils 200, 400 for a predetermined duration sufficient to partially melt the resilient foam material portions of spacer 300 that are in contract with the foils 200, 400. The heated surfaces are removed from contact with the foils 200, 400 after the predetermined heat cycle duration, and then the top and bottom flexible foils are placed in contact with and between two cooling plates (not shown) that have a predetermined low temperature. The resilient unitary foam spacer is then compressed between both the top and bottom foils and the positive cooling plates for a predetermined duration sufficient to solidify the melted resilient foam material portions of the spacer 300 that are in contract with the top and bottom foils. The thickness of spacer 300 at points of contact with foil 200, 400 before heating is 0.125 inches (0.03 mm) and is 0.090 inches (0.02 mm) after melting of the foam interior.

The result of this successive heating and cooling operation is to sealingly join the top and bottom foils 400, 200 to the resilient foam unitary member or spacer 300. Alternatively, if the above spacer-to-foil melting procedure is not used, a simple biologically inert adhesive can be applied between the spacer and the foils so as to seal the fluid passageway.

As seen in FIG. 2, top layer 400 comprises essentially the same shape as spacer 300 and layer 200. However, the only shaping requirement for layer 400 is for the serpentine path to be completely covered. The peripheral edge 402 of layer 400 should be reasonably free of edges which provide opportunity for catching and tearing. The combined thickness of bottom foil 200, spacer 300, and top foil 400 is greater than the thickness of ledge 114 such that when frame 100, bottom foil 200, spacer 300 and top foil 400 are assembled to form cassette 20, the top side 404 of layer 400 is accessible by the bottom 22 of an associated planar top heating plate 12, as shown in FIG. 7. Bottom surface 22 of top plate 12 is flat to compressively and fully contact the top surface 404 of layer 400.

Spacer 300 has spacer holes 328 for inserting therethrough shims 330. Shims 330 serve to maintain the top heating block 12 and the bottom heating blocks 14 substantially parallel and at a constant plate separation distance. This separation distance enables the top and bottom heating blocks 12, 14 to compress, at least in part, the resilient foam unitary member or spacer 300 such that the pressure within the serpentine flow path 308 will prevent the formation of gaseous bubbles on the top and bottom foils 400, 200, both of which act as heat conductive membrane means. It is well known in the art that lower than ambient pressures result in outgassing from parenteral fluids which provoke the formation of bubbles along a flow path. In some cases, distortion of plastic bags and other flexible containers in some heaters create such negative pressures with resulting bubble formation. Bubbles disposed across an otherwise useful thermal conductive path significantly reduce heater efficiency. The higher than ambient static pressure within cassette 20 reduces outgassing and formation of bubbles within the flow path 308.

Referring to FIG. 7, a cross section of a portion of heating assembly 10 is seen wherein the heating plates 12 and 14 are tightly clamped upon cassette 20, making firm contact above and below supports provided by shims 330 and supporting parts of the cassette 20. The supporting parts comprise path separators 310 (shown in FIG. 2). In the vicinity of each separator 310, close contact is maintained between the upper surface 404 of layer 400 and the bottom surface 22 of heating plate 12 and the lower surface 206 of layer 200 and the top surface 82 of bottom heating plate 14.

As seen in FIG. 2, frame 100 also comprises a handle 140. Handle 140 provides a hand hold for a user in handling cassette 20 and for use in inserting cassette 20 between heating plates 12 and 14, as shown in FIGS. 1 and 7.

Referring again to FIG. 7, cassette 20 is disposed between top heating plate 12 and bottom heating plate which, in combination with cassette 20, comprise three of the components of heating assembly 10. Top heating plate 12 is reciprocally moved up and down as shown by arrow 16 to release and make pressurized contact with cassette 20. Bottom heating plate 14 provides a static mounting surface for cassette 20.

Bottom plate 14 comprises a planar top surface 82. Planar top surface 82 comprises a shape which conforms to the size and shape of frame 100, as seen in FIGS. 1 and 7, such that when cassette 20 is set upon bottom plate 14 surface 82 nests within the medial access area of frame 100 and directly contacts surface 206 of layer 200. Specifically, the medial access area of frame 100 comprises the area defined by proximal end support 168, right bottom plate stop 144, left bottom plate stop 124, distal end support bottom 108, right frame alignment rail 105, and left frame alignment rail 103.

The top plate 12 and the bottom plate 14 are preferably constructed of copper. The bottom surface 84 of the top plate 12 and the top surface 82 of the bottom plate 14 preferably have a 0.0005 inch (0.81 mm) chrome plating, respectively 460, 260 thereon to avoid problems of oxidation and the lack of surface evenness therefrom. Alternatively, each plate 12, 14 may have a surface of hard anodized aluminum oxide. Each plate 14, 12 has respectively, a plate holder 608, 610 to support the plate and to serve as a handle to withdraw the plate from the parenteral fluid heating assembly 10 for servicing.

The top surface 83 of the top plate 12 and the bottom surface 81 of the bottom plate 14 preferably have a heating means thereon for generating at each plate 12, 14 a gradation of heat energy such that more heat energy is available for transfer to the parenteral fluid at the inlet end 318 of the serpentine flow path 308 within the first flow path zone 335, than is available for transfer to the parenteral fluid at the outlet end 316 of the serpentine flow path 308 within the third flow path zone 331.

In a preferred embodiment, the heating elements 584, 574 on each plate, 12, 14, each have three heating zones that correspond to zones 335, 333 and 331 of passage 308 (see FIG. 2). The heating zones of heating elements 584, 574 are shown in FIGS. 5 and 6. Each of the heating zones correspond by position to the zones 335, 333, 331 of serpentine path 308 in that they are immediately either over or under a specific section of serpentine path 308. In other words, each of the heating zones of heating elements 584, 574 are situated in a horizontal plane in contact with the respective plate or heating block 12, 14 and are substantially confined within an area defined by and immediately vertically offset from the open medial section or flow passageway 308 of the spacer 300. Specifically, heat zone 534 of the top plate 12 and heat zone 535 of the bottom plate 14 both correspond with the first flow path zone 335. Heat zone 533 of the top plate 12 and heat zone 532 of the bottom plate 14 both correspond with the second flow path zone 333. Heat zone 531 of the top plate 12 and heat zone 530 of the bottom plate 14 both correspond with the third flow path zone 331.

Each of the three heating zones has a single electrically conducting strip on each of the two heating blocks or plates 12, 14, in electrical connection with a power source 614. Thus, there are three sections of heat stripping 574 on bottom plate 14 and three sections of heat stripping 584 on top plate 12. Each strip is arranged so that the beginning, middle and end of the strip are all situated close to the same lengthwise end of the spacer 300. Specifically, the bottom plate 14 has the beginning 523, middle 567, and end 519 of the heat strip in the first heat zone 535 close to the distal end of plate 14. The bottom plate 14 also has the beginning 515, middle 565, and end 511 of the heat strip in the second heat zone 533 close to the distal end of plate 14. Lastly, bottom plate 14 has the beginning 505, middle 563, and end 503 of the heat strip in the third heat zone 531 close to the distal end of plate 14. The top plate 12 is similar in that it has near its distal end the beginning 522, middle 568, and end 518 of the heat strip in the first heat zone 534. The top plate 12 also has the beginning 514, middle 566, and end 510 of the heat strip in the second heat zone 532 near the top plate 12 distal end. Lastly, top plate 12 has near its distal end the beginning 506, middle 564, and end 502 of the heat strip in the third heat zone 530.

The heat strip in each heating zone comprises a thin electrical conductor and is preferably a foil heating element having an approximate thickness of 0.0009 inches (0.0229 mm). When properly arranged on a heating plate, the power density of the area covered by the heat strip is varied end to end of the strip so as to provide an area of greatest heat output where heat absorption by the parenteral fluid flowing through cassette 20 is the greatest (i.e. at the input). The heat strip may be a flexible thermofoil heating element or a glass reinforced silicon rubber heater manufactured and distributed by Minco Products, Inc., 7300 Commerce Lane, Minneapolis, Minn. 55432.

In diagrammatic summary, Table 1.1 is presented to depict each of the three heating zones and with associated reference numerals to the Figures. Each heating zone has been divided into halves. The preferred average power density and preferred area is shown in Table 1.1 for each half of each heat zone. Additionally, the approximate power for each heating zone at 120 volts is given.

TABLE 1.1

|  | HEAT ZONE NUMBER | | |
| --- | --- | --- | --- |
|  | 1 | 2 | 3 |
| TOP PLATE HEATING STRIP | 534 | 533 | 531 |
| FLOW PATH ZONE | 335 | 333 | 331 |
| BOTTOM PLATE HEATING STRIP | 535 | 532 | 530 |
| FIRST HALF AVERAGE POWER DENSITY (W/IN$^2$) | 46.5 | 37.5 | 24.5 |
| SECOND HALF AVERAGE POWER DENSITY (W/IN$^2$) | 43.0 | 30.5 | 18.5 |
| FIRST HALF AREA (IN$^2$) | 4.46 | 4.01 | 4.01 |
| SECOND HALF AREA (IN$^2$) | 4.01 | 4.01 | 4.46 |
| POWER AT 120 VOLTS (W) | 380 | 272 | 180 |

Each heat strip comprises sufficient heat capacity to provide a homogenous temperature at the interface, yet is sufficiently thin to provide a rapid thermal response to bottom and top foils 200, 400.

With respect to both the heat strips of the plates 12, 14 and to the serpentine passageway 308 of spacer 300, fluid enters the cassette 20 through inlet tube 110 at top plate point 562, bottom plate point 595, and at spacer point 318. Fluid exits the cassette 20 through outlet tube 120 at top plate point 564, bottom plate point 563, and at spacer point 316.

All of the heating strips are fixed to their respective heating block or plate 12, 14 by a combination rubber and adhesive mixture. Both the heating strips and rubber-adhesive mixture are covered over with a layer of rubber-like material to form a rubber-like mat. As shown in FIG. 7, the top heat plate 12 has mounted thereon a rubber-like mat 580 comprising a rubber-like material 582 with a double sided adhesive coating thereon which is secured to the top of the top plate 12. The double sided adhesive adheres the rubber-like material 582 to both the top plate 12 and to the three heat strips 584 which are on top of the rubber-like mat 582. On top of the rubber-like material 582 is adhesive coating 586. On top of adhesive coating 586 is another rubber-like material 588. Likewise, the bottom heat plate 14 has mounted thereon a rubber-like mat 570 comprising a rubber-like material 572 with a double sided adhesive coating thereon which is secured to the bottom of plate 14. The double sided adhesive adheres the rubber-like material 572 to both the bottom plate 14 and to the three heat strips 574 which are on the bottom of the rubber-like material 572. On the bottom of the rubber-like material 572 is adhesive coating 576. On the bottom of the adhesive coating 576 is another rubber-like material 578. The rubber-like materials 572, 578, 582, and 588 can also have a woven fabric therein so as to add to the respective rubber mats 570, 580 strength and stability, as well as thermal mass. Preferably, rubber-like materials 572, 578, 582, 588 are 0.008 inch (0.020 mm) fiberglass reinforced silicone rubber.

The arrangement of the heat strips 584, 574 on each plate 12, 14 is such that each strip in each heating zone is divided into a plurality of contiguous, alternatingly perpendicular sections. Each section of each heating strip has a parallel section with a conductor separation distance therebetween. As shown respectively in FIGS. 5 and 6, heat strip section 540 on the top plate 12 has a closest parallel section 542 on the top plate 12, and heat strip section 536 on the bottom plate 14 has a closest parallel section 538 on the bottom plate 14. Both the width and the electrical resistance of the heat strip is substantially constant within each heating zone. However, within each heating zone, the conductor separation distance increases. The effect of the increase in the conductor separation distance is that there is a decrease in the power density for the area defined by the heat strip section and its corresponding closest parallel section. In turn, a decrease in power density in the respective heating zones will transfer progressively less heat to the fluid in the fluid passageway 308. In other words, from the inlet end 318 of the serpentine flow path 300 to the outlet end 316 of the serpentine flow path 308, the electrical power density transmitted from the heat strips through the plates 12, 14, to the fluids within said serpentine flow path 308 decreases. The profiled shape and arrangement of the heating strips, as shown in FIGS. 5 and 6, are such that, relatively and progressively, within each heating zone, from the beginning of the heat strip to the end of the heat strip, the conductor separation distance increases, the electrical power density decreases, and for the area defined by the conductor separation distance, the section of the heating strip and the corresponding closest parallel section of the heating strip, the electrical power density decreases. Further, the electrical power density decrease is substantially linear within each heating zone.

The heat strips are individually arranged both immediately above and below the serpentine flow path 308 in a substantially mirror image to the serpentine flow path 308, as shown in FIGS. 2, 5, and 6.

Depicted in FIGS. 5 and 6 is a heat strip arrangement where the electrical power density near the end points 518, 519 of the respective heat strips in the first heating zones 534, 535 is less than the electrical power density at the beginning points 514, 515 of the respective heat strips of the second heating zones 532, 533. Additionally, the electrical power density near the end points 510, 511 of the respective heat strips in the second heating zones 532, 533 is less than the electrical power density at the beginning points 505, 506 of the respective heat strips of the third heating zones 530, 531.

The electrical resistance of the heating strip within each of the heating zones is substantially constant. However, the resistance decreases from one heating zone to the next. Specifically, the heating strip resistance for heating zone decreases from a point in the first heating zones 534, 535 that is vertically offset from and horizontally aligned with the inlet end 318 of the serpentine flow path 308 to a point on the third heating zones 530, 531 that is vertically offset from and horizontally aligned with the outlet end 316 of the serpentine flow path 308, such that there is provided differing energy outputs and a gradation of heat energy to the fluids within said serpentine flow path 308.

Figure 3:
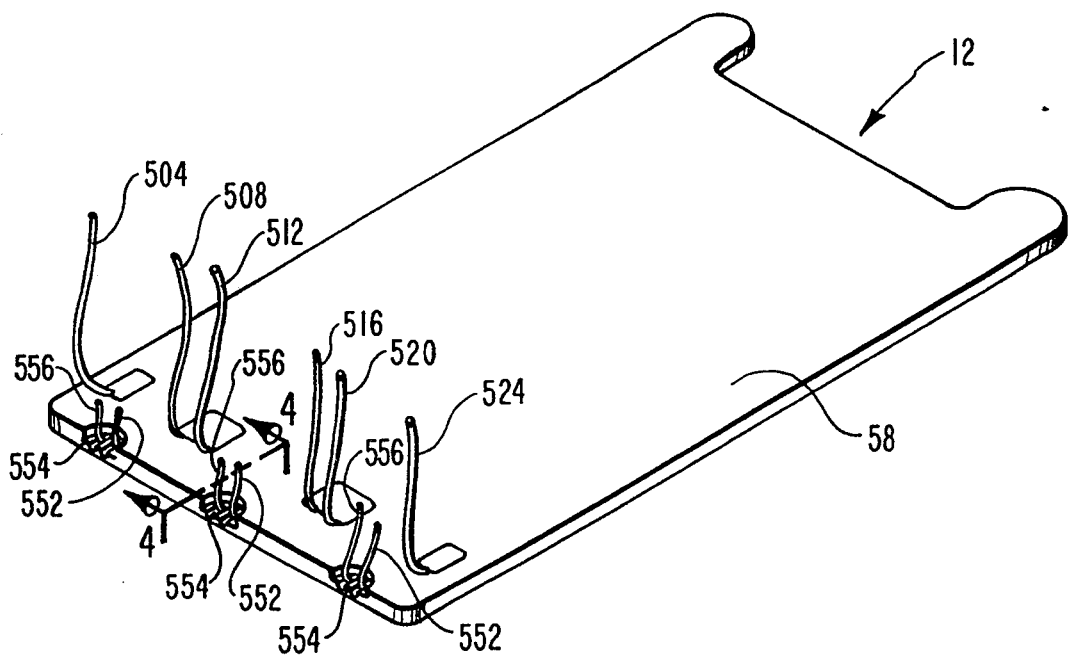
FIG. 3 is a perspective view of the top heating plate showing electrical leads to sensors and to profiled electrically conducting strips.
Figure 4:
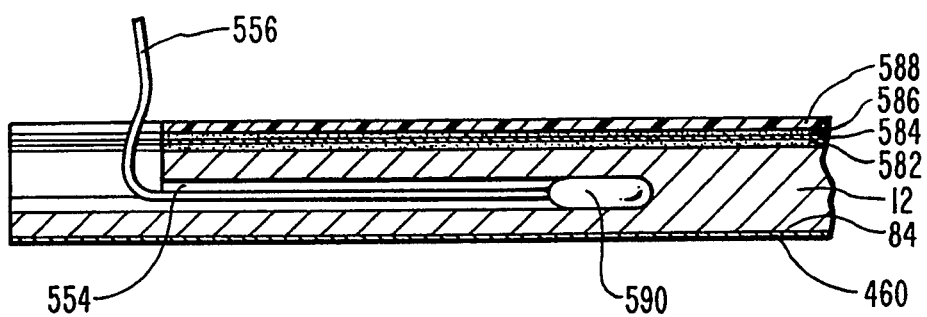
FIG. 4 is a sectional view along lines 4—4 of FIG. 3.

Each heat strip has at least one sensor means associated therewith for deriving the temperature at a point within the elongate flow path 308. By way of example as illustrated in FIGS. 3 and 4, the top plate 12 has, for each heat strip in each heating zone 530, 532, 534 a heat sensor 590. Each heat sensor 590 detects the temperature at a point within each respective heating zone. The heat sensor 590 can be a thermocouple, thermistor, or other device that is within the skill of the artisan for such uses. The heat sensors shown are installed within the top plate 12 by a drilled hole 554 in the top plate 12. Each heat sensor 590 has two electrical leads 552, 556 which serves to communicate an electrical signal, proportional to the sensed temperature to a controller/power source 614 within the parenteral fluid heater assembly 10. In the preferred embodiment, the bottom plate 14 has, for each heating zone 531, 533, 535 a heat sensor like that shown at 590 that is installed in a similar way. A heat sensor 590, for both top 12 and bottom 14 plates is installed roughly in the middle of each heating zone.

The inventive fluid heating apparatus further comprises a means for automatically controlling the heat output by each heat strip relative to a selected temperature as a function of the temperature derived from the heat sensor at each respective point within the elongated flow path, whereby the temperature of the fluid at the outlet end of the flow path is controlled to be substantially equal to the selected set point temperature. An example of such an automatic controlling means is given for the purpose of illustration in FIG. 1 generally indicated at 614 as the controlling power source. The controller/power source 614 is a means for automatically controlling the temperature of the fluids at the outlet end 316 of the serpentine flow path 308 based upon a selected temperature that is stored in the controller/power source 614 and upon each detected temperature at each heat sensor 590. The controller may be a micro-controller with a memory, an A/D converter, and a micro-processor by which an electrical control system for regulating temperature is programmably controlled. Identical thermal control interfacing circuits are provided for top heating plate 12 and bottom heating plate 14. For this reason, only the thermal control for top heating plate 12 is described.

The controller/power source 614, after receiving signals from leads 552, 556, regulates the power to heating zones 530 through 535 through respective electrical leads to each respective heat strip. As shown in FIG. 3, the top plate 12 has electrical leads 520 and 524 connected to the first heating zone 534, with leads 516, 512 connected to the second heating zone 532, and leads 508, 504 connected to the third heating zone 530. The bottom plate 14, has similar leads to similar heat strips and respective heating zones as that of the plate 12.

The inventive fluid warmer further comprises a resilient biasing means for forcing vertically downwards the top plate 12 against the shims 330 towards the bottom plate 14, whereby the top plate 12 is forced vertically upwards by both the resilient foam spacer 300 and the fluid in the flow path 308, and the top plate 12 floats under the effect of the vertical forces. As an example to illustrate a preferred embodiment of the resilient biasing means FIG. 7 depicts a pneumatic bag 52 that serves as an articulating joint capable of performing the recited function. As shown in FIG. 7, the plate holder 610 for the top plate 12 has in contact therewith the pneumatic bag 52 which allows the plane of surface 22 of cop heating plate 12 to conform to %he plane of each cassette 20 disposed thereunder by the movement of the pneumatic bag 52. The bag 52 is inflatable bag, and upon inflation, the plate holder 610 is lowered so as to compressively sandwich cassette 20 between heating plates 12 and 14.

The bag 52 is in pneumatic communication with air tube 54 which connects to a pneumatic source (not shown) so as to both inflate and deflate the bag 52. Other means of compressively sandwiching cassette 20 between heating plates 12 and 14 that are equivalents to that illustrated herein are also contemplated as within the scope of the present invention.

The plate holder 608 for the bottom plate 14 is static and does not move vertically. The plate holder 608 is sized and shaped to releasably accept insertion of bottom heating plate 14 and provides static support for bottom heating plate 14 and therefore for cassette 20 when residing upon heating plate 14 and for top heating plate 12 when it is compressively lowered to rest upon cassette 20.

Controller/power source 614 further comprises a control panel 616 whereby a user controls insertion and extraction of cassette 20 and ascertains the status of parenteral fluid warmer 10 in operation. Additionally, control panel 614 further comprises the user interface for the electrical control system of the parenteral fluid warming system 10.

It will be appreciated that the electronic control functions described in the above disclosure could be provided any digital processor, such as a microprocessor or a personal computer. Such a processor may be programmed so as to implement the above-described functions using any one of a variety different programming languages and programming techniques. Attached hereto as Appendix A is one such program which was prepared for use with a microprocessor and circuit configuration appropriate for controlling the disclosed profiled heat elements and other components associated with the operation of the inventive fluid warmer. The attached program comprises a listing of source code for the microprocessor, which in the presently preferred embodiment, may be a general purpose microcomputer such as an IBM Personal Computer or an equivalent device. Alternatively, it may be desirable to utilize a more powerful microcomputer or to devise a microprocessor-based apparatus specifically designed to carry out the data processing functions incidental to this invention.

Importantly, the hardware which embodies the processor means of the present invention must function to perform the operations essential to the invention and any device capable of performing the necessary operations should be considered an equivalent of the processor means. As will be appreciated, advances in the art of modern electronic devices may allow the processor means to carry out internally many of the functions carried out by hardware as being independent of the processor means. The practical considerations of cost and performance of the system will generally determine the delegation of functions between the processor means and the remaining dedicated hardware.

The processor of the presently preferred embodiment is interconnected with the remaining apparatus hardware by way of I/O ports and a plurality of analog to digital converters. Also, a visual display on control panel 616 is connected to the processor. The visual display performs the function of a display means. As intended herein, the display means may be any device which enables the operating personnel to observe the values calculated by the microcomputer. Thus, the display means may be a device such as a cathode ray tube, an LCD display, a chart recorder, or any other device performing a similar function.

The method of the present invention is carried out under the control of a program resident in the processor. Those skilled in the art, using the information given herein, will readily be able to assemble the necessary hardware, either by purchasing it off-the-shelf or by fabricating it and properly programming the processor. While it is desirable to utilize clock rates that are as high as possible and as many bits as possible in the A/D converters, the application of the embodiment and economic considerations will allow one skilled in the art to choose appropriate hardware for interfacing the processor with the remainder of the embodiment. Also, it should be understood that for reasons of simplifying the diagrams, power supply connections, as well as other necessary structures, are not explicitly shown in the figures, but are provided in actuality using conventional techniques and apparatus.

For reasons of safety, an isolation transformer circuit (not shown) should be used in combination with the inventive fluid warmer. In a preferred embodiment, the A/C voltage is specified at 117 volts, the current is at 15 amps, and leakage current is specified to be at a maximum of 30 microamps. It is intended that the isolation transformer be used to isolate the inventive fluid warmer from its power source so that the inventive fluid warmer circuits derive power from the power source without a continuous wire connection between them. In this way, a fault occurring in the power source, or a current leakage, will not injure the patient. In operation, the power supply of the fluid warmer is plugged into the isolation transformer and the isolation transformer is plugged into an A/C power source.

Before using the parenteral fluid warmer 10, the cassette 20 must be in place, interposed between top heating plate 12 and bottom heating plate 14 within the parenteral fluid warmer 10. Before inserting cassette 20, plate holder 610 and top plate 12 must be raised. The raising and lowering of the plate holder 610 and top plate 12 are controlled by user interfacing with control panel 616 and controller/power source 614 in combination with electrical circuitry which alternatively increases and relieves pressure communicating through an electrically controlled pneumatic valve to a compressed air source so as to provide pressurized fluid to drive inflatable air bag 52 by air line 54. Air bag 52 could also comprise a spring or otherwise powered return which retracts and closes the plate holder 610 and thereby raises or lowers top plate 12.

With cassette 20 disposed in the fluid warmer 10, connection is made with one or more parenteral fluid sources 600, 602 in a fluid pressurizing source as seen schematically in FIG. 1, and fluid delivery then begins after setting the appropriate set point and other control parameters.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. An apparatus for heating fluids comprising:
   a cassette means for transferring heat to fluids flowing therethrough, the cassette means comprising:
   passageway means for defining a thin, planar, elongated, sinuous flow path having first and second sides and an inlet end and an outlet end, such that a thin sheet of fluid enters the inlet end, travels through the flow path, and exits the outlet end;
   a first flexible, heat conductive membrane means supported by the passageway means on one of the first or second sides of the flow path, for providing heat transfer to one of the top and bottom sides of the flow path; and
   a second flexible, heat conductive membrane means supported by the passageway means on the other of the first or second sides of the flow path for providing heat transfer to the other of the first and second sides of the flow path; and
   heating means in contact with at least one of said first and second heat conductive membrane means for generating heat energy, said heating means comprising a heating element means for generating a gradation of heat energy such that more heat energy is available for transfer to the parenteral fluid at the inlet end of the sinuous flow path than is available for transfer to the parenteral fluid at the outlet end of the sinuous flow path, having a shape that is essentially a mirror image of the elongated sinuous flow path, and the heating element means being spaced from and in alignment with at least one of the first or second sides of the elongated flow path.

2. An apparatus as defined in claim 1 wherein said heating element means comprises an electrically conductive strip with a beginning and an end, said electrically conductive strip comprising a plurality of perpendicular sections, each said perpendicular section having a conductor separation distance therebetween, and wherein progressively for the perpendicular sections from the beginning of said electrically conductive strip to the end of said strip the electrical power density decreases.

3. An apparatus as defined in claim 2 wherein said progressive conductor separation distance increase and said progressive electrical power density decrease are substantially linear from said beginning to said end.

4. An apparatus as defined in claim 2 wherein said elongated flow path has a plurality of pairs of contiguous first and second longitudinal segments, each of said first and second longitudinal segments having a beginning point and an ending point, and wherein relatively within an area defined by each of said pairs, the electrical power density progressively decreases from the beginning point of each said first longitudinal segment to the ending point of the corresponding second longitudinal segment.

5. An apparatus as defined in claim 4 wherein said progressive electrical power density decrease is substantially linear.

6. An apparatus as defined in claim 2 wherein the cross-sectional area of said electrically conductive strip is substantially constant.

7. An apparatus as defined in claim 2 wherein the electrical resistance of said electrically conductive strip is substantially constant.

8. An apparatus as defined in claim 2, further comprising at least one heat sensor means for detecting the temperature at a point within said elongated flow path.

9. An apparatus as defined in claim 8 wherein said at least one heat sensor means comprises a thermistor.

10. An apparatus as defined in claim 8 further comprising means for automatically controlling the heat output by said electrically conductive strip relative to a selected temperature as a function of each said derived temperature at each said point within said elongated flow path, whereby the temperature of the fluid at the outlet end of the flow path is controlled to be substantially equal to said selected temperature.

11. An apparatus as defined in claim 2 wherein said heating element means comprises a second electrically conducting strip, each said electrically conductive strip providing heat energy for transfer to one of the first and second heat conductive membranes.

12. An apparatus as defined in claim 2, wherein said heating means further comprises a thermally conductive heating block having first and second opposite planar sides, said electrically conductive strip being disposed on said first side of the heating block, and said second side of heating block contacting one of said first and second flexible, heat conductive membrane means, whereby said electrically conductive strip transfers heat to the fluid within said elongated flow path through the first side of said heating block.

13. An apparatus as defined in claim 11, wherein said heating means further comprises a pair of thermally conductive heating blocks each having first and second opposite planar sides, each said electrically conductive strip being respectively disposed on said first side of one of said heating blocks, and said second side of each heating block in said pair of heating blocks contacting one of said first and second flexible, heat conductive membrane means, whereby each said electrically conductive strip transfers heat to the fluid within said elongated flow path through the first side of one of said heating blocks.

14. An apparatus as defined in claim 13 wherein said passageway means is comprised of a thermally insulating material that has a plurality of shims for maintaining said second sides of said heating blocks substantially relatively parallel and at a minimum separation distance.

15. An apparatus as defined in claim 14 wherein said material is polyethylene.

16. An apparatus as defined in claim 14, further comprising a resilient biasing means for forcing one of said heating blocks against said plurality of shims towards the other said heating block, whereby said other heating block floats under the effect of countervailing forces provided by the resilient foam material and the fluid in said elongated flow path.

17. An apparatus as defined in claim 16 wherein said resilient biasing means comprises an inflatable bag situated adjacent to said one of said heating blocks.

18. An apparatus as defined in claims 1 or 14 wherein said first and second flexible, heat conductive membrane means are sealingly joined to said passageway means by heating said first and second heat conductive membrane means in contact with said passageway means sufficient to partially melt the portions of said passageway means in contact with said first and second membrane means.

19. An apparatus as defined in claims 1 or 14 wherein said first and second flexible, heat conductive membrane means are made substantially from metallic foil.

20. An apparatus as defined in claim 19 wherein said metallic foil is stainless steel foil.

21. An apparatus for heating parenteral fluids for intracorporeal delivery to a patient, comprising:
   a cassette means for transferring heat to parenteral fluids flowing therethrough, the cassette means comprising:
      passageway means having top and bottom sides and defining a thin, planar elongated, sinuous flow path having top and bottom sides and an inlet end and an outlet end, such that a thin sheet of parenteral fluid enters the inlet end, travels through the flow path, and exits the outlet end;
      a first flexible, heat conductive membrane means supported on one of the top or bottom sides of the passageway means and providing heat transfer to one of the top and bottom sides of the flow path; and
      a second flexible, heat conductive membrane means supported on the other of the top or bottom sides of the passageway means, and providing heat transfer to the other of the top and bottom sides of the flow path, said passageway means holding the first and second conductive membranes means in spaced relation one from the other; and
   a heating means in contact with one of said first and second heat conductive membrane means for generating heat energy for transfer to the parenteral fluid in the elongated flow path, said heating means comprising:
      a first and a second heating element means for generating a gradation of heat energy such that more heat energy is available for transfer to the parenteral fluid at the inlet end of the sinuous flow path than is available for transfer to the parenteral fluid at the outlet end of the sinuous flow path, each heating element means having a shape that is essentially a mirror image of the elongated sinuous flow path, said first heating element means being disposed essentially both vertically offset from and in alignment with said top side of the elongated flow path, said second heating element means being disposed essentially both vertically offset from and in alignment with said bottom side of the elongated flow path.

22. An apparatus as defined in claim 21 wherein each said heating element means comprises an electrically conductive strip with a beginning and an end, said electrically conductive strip comprising a plurality of perpendicular sections, each said perpendicular section having a conductor separation distance therebetween, and wherein progressively for the perpendicular sections from the beginning of said electrically conductive strip to the end of said strip the electrical power density decreases.

23. An apparatus as defined in claim 22 wherein said progressive conductor separation distance increase and said progressive electrical power density decrease are substantially linear from said beginning to said end.

24. An apparatus as defined in claim 22 wherein said elongated flow path has a plurality of pairs of contiguous first and second longitudinal segments, each of said first and second longitudinal segments having a beginning point and an ending point, and wherein relatively within an area defined by each of said pairs, the electrical power density progressively decreases from the beginning point of each said first longitudinal segment to the ending point of the corresponding second longitudinal segment.

25. An apparatus as defined in claim 24 wherein said progressive electrical power density decrease is substantially linear.

26. An apparatus as defined in claim 22 wherein the cross-sectional area of each said electrically conductive strip is substantially constant.

27. An apparatus as defined in claim 22 wherein the electrical resistance of each said electrically conductive strip is substantially constant.

28. An apparatus as defined in claim 22, further comprising at least one heat sensor means for detecting the temperature at a point within said elongated flow path.

29. An apparatus as defined in claim 28 wherein said at least one heat sensor means comprises a thermistor.

30. An apparatus as defined in claim 28 further comprising means for automatically controlling the heat output by each said electrically conductive strip relative to a selected temperature as a function of each said derived temperature at each said point within said elongated flow part, whereby the temperature of the parenteral fluids at the outlet end of the flow path is controlled to be substantially equal to said selected temperature.

31. An apparatus as defined in claim 22, wherein said heating means further comprises a pair of thermally conductive heating blocks each having first and second opposite planar sides, each said electrically conductive strip being respectively disposed on said first side of one of said heating blocks, and said second side of each heating block in said pair of heating blocks contacting one of said first and second flexible, heat conductive membrane means, whereby each said electrically conductive strip transfers heat to the parenteral fluid within said elongated flow path through the first side of one of said heating blocks.

32. An apparatus as defined in claim 31 wherein said passageway means is comprised of a thermally insulating material that has a plurality of shims for maintaining said second sides of said heating blocks substantially relatively parallel and at a minimum separation distance.

33. An apparatus as defined in claim 32 wherein said material is polyethylene.

34. An apparatus as defined in claim 32, further comprising a resilient biasing means for vertically forcing downwards one of said heating blocks against said plurality of shims towards the other said heating block, whereby said other heating block floats under the effect of countervailing forces provided by the resilient foam material and the fluid in said elongated flow path.

35. An apparatus as defined in claim 34 wherein said resilient biasing means comprises an inflatable bag situated vertically above and forcing downwardly on said one of said heating blocks.

36. An apparatus as defined in claims 21 or 32 wherein said first and second flexible, heat conductive membrane means are sealingly joined to said passageway means by heating said first and second heat conductive membrane means in contact with said passageway means sufficient to partially melt the portions of said passageway means in contact with said first and second membrane means.

37. An apparatus as defined in claims 21 or 32 wherein said first and second flexible, heat conductive membrane means are made substantially from metallic foil.

38. An apparatus as defined in claim 37 wherein said metallic foil is stainless steel foil.

39. An apparatus for heating parenteral fluids for intracorporeal delivery to a patient, comprising:
  a cassette means for transferring heat to parenteral fluids flowing therethrough, the cassette means comprising:
    passageway means having top and bottom sides and defining a thin, planar, elongated, sinuous flow path having top and bottom sides and an inlet end and an outlet end, such that a thin sheet of parenteral fluid enters the inlet end, travels through the flow path, and exits the outlet end;
    a first flexible, heat conductive membrane means supported on one of the top or bottom sides of the passageway means and providing heat transfer to one of the top and bottom sides of the flow path; and
    a second flexible, heat conductive membrane means supported on the other of the top or bottom sides of the passageway means, and providing heat transfer to the other of the top and bottom sides of the flow path, said passageway means holding the first and second conductive membrane means in spaced relation one from the other; and
  a heating means in contact with at least one of said first and second heat conductive membrane means for generating heat energy, said heating means comprising:
    a heating element means for generating a gradation of heat energy such that more heat energy is available for transfer to the parenteral fluid at the inlet end of the elongated flow path than is available for transfer to the parenteral fluid the outlet end of the elongated flow path, said heating means having a shape that is essentially mirror image of the elongated sinuous flow path, and the heating element means being disposed essentially both vertically offset from and in alignment with at least one of the top or bottom sides of the elongated flow path.

40. An apparatus as defined in claim 39 wherein said heating element means comprises an electrically conductive strip with a beginning and an end, said electrically conductive strip comprising a plurality of perpendicular sections, each said perpendicular section having a conductor separation distance therebetween, and wherein progressively for the perpendicular sections from the beginning of said electrically conductive strip to the end of said strip the electrical power density decreases.

41. An apparatus as defined in claim 40 wherein said progressive conductor separation distance increase and said progressive electrical power density decrease are substantially linear from said beginning to said end.

42. An apparatus as defined in claim 40 wherein said elongated flow path has a plurality of pairs of contiguous first and second longitudinal segments, each of said first and second longitudinal segments having a beginning point and an ending point, and wherein relatively within an area defined by each of said pairs, the electrical power density progressively decreases from the beginning point of each said first longitudinal segment to the ending point of the corresponding second longitudinal segment.

43. An apparatus as defined in claim 42 wherein said progressive electrical power density decrease is substantially linear.

44. An apparatus as defined in claim 40 wherein the cross-sectional area of said electrically conductive strip is substantially constant.

45. An apparatus as defined in claim 40 wherein the electrical resistance of said electrically conductive strip is substantially constant.

46. An apparatus as defined in claim 40, further comprising at least one heat sensor means for detecting the temperature at a point within said elongated flow path.

47. An apparatus as defined in claim 46 wherein said at least one heat sensor means comprises a thermistor.

48. An apparatus as defined in claim 46 further comprising means for automatically controlling the heat output by said electrically conductive strip relative to a selected temperature as a function of each said derived temperature a each said point within said elongated flow path, whereby the temperature of the fluid at the outlet end of the flow path is controlled to be substantially equal to said selected temperature.

49. An apparatus as defined in claim 40 wherein said heating element means comprises a second electrically conducting strip, each said electrically conductive strip providing heat energy for transfer to one of the first and second heat conductive membranes.

50. An apparatus as defined in claim 40, wherein said heating means further comprises a thermally conductive heating block having first and second opposite planar sides, said electrically conductive strip being disposed on said first side of the heating block, and said second side of heating block contacting one of said first and second flexible, heat conductive membrane means, whereby said electrically conductive strip transfers heat to the fluid within said elongated flow path through the first side of said heating block.

51. An apparatus as defined in claim 49, wherein said heating means further comprises a pair of thermally conductive heating blocks each having first and second opposite planar sides, each said electrically conductive strip being respectively disposed on said first side of one of said heating blocks, and said second side of each heating block in said pair of heating blocks contacting one of said first and second flexible, heat conductive membrane means, whereby each said electrically conductive strip transfers heat to the fluid within said elongated flow path through the first side of one of said heating blocks.

52. An apparatus as defined in claim 51 wherein said passageway means is comprised of a thermally insulating material that has a plurality of shims for maintaining said second sides of said heating blocks substantially relatively parallel and at a minimum separation distance.

53. An apparatus as defined in claim 52 wherein said material is polyethylene.

54. An apparatus as defined in claim 52 further comprising a resilient biasing means for forcing one of said heating blocks against said plurality of shims towards the other said heating block, whereby said other heating block floats under the effect of countervailing forces provided by the resilient foam material and the fluid in said elongated flow path.

55. An apparatus as defined in claim 54 wherein said resilient biasing means comprises an inflatable bag situated adjacent to said one of said heating blocks.

56. An apparatus as defined in claims 39 or 52 wherein said first and second flexible, heat conductive membrane means are sealingly joined to said passageway means by heating said first and second heat conductive membrane means in contact with said passageway means sufficient to partially melt the portions of said passageway means in contact with said first, and second membrane means.

57. An apparatus as defined in claims 39 or 52 wherein said first and second flexible, heat conductive membrane means are made substantially from metallic foil.

58. An apparatus as defined in claim 57 wherein said metallic foil is stainless steel foil.

59. An apparatus for heating parenteral fluids for intracorporeal delivery to a patient, comprising:
   a cassette means for transferring heat to parenteral fluids flowing therethrough, the cassette means comprising:
      passageway means having top and bottom sides and defining a thin, planar sinuous flow path having top and bottom sides and an inlet end and an outlet end, such that a thin sheet of parenteral fluid enters the inlet end, travels through the flow path, and exits the outlet end;
      a first thin, flexible metallic foil conductive membrane means supported on one of the top or bottom sides of the passageway means and providing heat transfer to one of the top and bottom sides of the flow path; and
      a second thin, flexible metallic foil conductive membrane means supported on the other of the top or bottom sides of the passageway means, and providing heat transfer to the other of the top and bottom sides of the flow path, said passageway means holding the first and second thin, flexible metallic foil conductive membrane means in spaced relation one from the other; and
   heating means in contact with said first and second thin, flexible metallic foil conductive membrane means for generating heat energy, said heating means comprising:
      a first and a second heating element means for generating a gradation of heat energy such that more heat energy is available for transfer to the parenteral fluid at the inlet end of the serpentine flow path than is available for transfer to the parenteral fluid at the outlet end of the serpentine flow path, each of which has a shape that is essentially a mirror image of the serpentine flow path, said first heating element means being disposed essentially both vertically offset from and in alignment with said top side of the serpentine flow path, said second heating element means being disposed essentially both vertically offset from and in alignment with said bottom side of the serpentine flow path.

60. An apparatus as defined in claim 59 wherein each said heating element means comprises an electrically conductive strip with a beginning and an end, said electrically conductive strip comprising a plurality of perpendicular sections, each said perpendicular section having a conductor separation distance therebetween, and wherein progressively for the perpendicular sections from the beginning of said electrically conductive strip to the end of said strip the electrical power density decreases.

61. An apparatus as defined in claim 60 wherein said progressive conductor separation distance increase and said progressive electrical power density decrease are substantially linear from said beginning to said end.

* * * * *

UNITED STATES PATENT AND TRADEMARK OFFICE
CERTIFICATE OF CORRECTION

PATENT NO. : 5,381,510
DATED : January 10, 1995
INVENTOR(S) : DIXON FORD et al.

It is certified that error appears in the above-indentified patent and that said Letters Patent is hereby corrected as shown below:

Column 1, line 8, "U.S. Pat. No. 5,245,68" should be --U.S. Pat. No. 5,245,693--
    Column 1, line 55, after "Thus," insert --a--
    Column 2, line 31, after "inlet and" insert --outlet--

Column 9, line 2, after "heating plate" insert --14--
    Column 13, line 25, "cop" should be --top--
    Column 13, line 26, "%he" should be --the--

Column 19, line 63, after "fluid" insert --at--
    Column 19, line 65, after "essentially" insert --a--
    Column 20, line 45, "a" should be --at--

Signed and Sealed this

Twenty-sixth Day of September, 1995

*Attest:*

BRUCE LEHMAN

*Attesting Officer*     *Commissioner of Patents and Trademarks*